United States Patent [19]

Weber

[11] Patent Number: 5,075,217
[45] Date of Patent: Dec. 24, 1991

[54] LENGTH POLYMORPHISMS IN (DC-DA)$_n$·(DG-DT)$_n$ SEQUENCES

[75] Inventor: James L. Weber, Marshfield, Wis.

[73] Assignee: Marshfield Clinic, Marshfield, Wis.

[21] Appl. No.: 341,562

[22] Filed: Apr. 21, 1989

[51] Int. Cl.$^5$ .................. C12Q 1/68; C07H 15/12; C12N 15/00
[52] U.S. Cl. ......................................... 435/6; 536/27; 935/77; 935/78
[58] Field of Search ................. 435/6; 536/27; 935/77, 935/78

[56] References Cited

U.S. PATENT DOCUMENTS

| 4,582,788 | 4/1986 | Erlich | 435/6 |
|---|---|---|---|
| 4,623,619 | 11/1986 | Owerbach et al. | 435/6 |
| 4,666,828 | 5/1987 | Gusella | 435/6 |
| 4,681,840 | 7/1987 | Stephenson et al. | 435/6 |
| 4,683,194 | 7/1987 | Saiki et al. | 435/6 |
| 4,683,202 | 7/1987 | Mullis | 435/91 |
| 4,710,461 | 12/1987 | Komano et al. | 435/172.3 |
| 4,710,465 | 12/1987 | Weissman et al. | 435/91 |

FOREIGN PATENT DOCUMENTS 186271 10/1985 United Kingdom .
238329 3/1987 United Kingdom .

OTHER PUBLICATIONS

Weber, et al., "Genome Mapping", Cold Spring Harbor Meeting, Apr. 27–May 1, 1988.
Weber, et al., "Abundant New Class of Human DNA Polymorphisms", Am. J. Hum. Genet. 1989 44(3), pp. 388–396.
Aldridge, et al., "A Strategy to Reveal High-Frequency RFLPs Along the Human X Chromosome", Am. J. Hum. Genet. 36:546–564, 1984.
Botstein, et al., "Construction of a Genetic Linkage Map in Man Using Restriction Fragment Length Polymorphisms", Am. J. Hum. Genet. 32:314–331, 1980.
Braaten, et al., "Locations and Contexts of Sequences that Hybridize to Poly (dG-dT)·(dC-dA) in Mammalian Ribosomal DNAs and Two X-Linked Genes", Nucleic Acids Research, vol. 16, #3 1988.
Das, et al., "The Human Apolipoprotein C-II Gene Sequence Contains a Novel Chromosome 19-Specific Minisatellite in Its Third Intron", The Journal of Biological Chemistry 1987.
Gilliam, et al., "Isolation of Polymorphic DNA Fragments From Human Chromosome 4", Nucleic Acids Research, vol. 15, #4, 1987.
Gross, et al., "Chromatin Structure of the Potential Z-Forming Sequence (dT-dG)$_n$·(dC-dA)$_n$", J. Mol. Bio. (1985) 183.251-265.
Gross, et al., "The Ubiquitous Potential Z-Forming Sequence of Eucaryotes, (dT-dG)$_n$·(dC-dA)$_n$, Is Not Detectable in the Genomes of Eubacteria, Archaebacteria, or Mitrochondria", Molecular and Cellular Biology, Aug. 1986 pp. 3010–3013.
Hamada, et al., "Potential Z-DNA Forming Sequences are Highly Dispersed in the Human Genome", Nature vol. 298, Jul. 22, 1982.
Hamada, et al., "A Novel Repeated Element with Z-DNA-Forming Potential is Widely Found in Evolutionarily Diverse Eukaryotic Genomes", Proc. Natl. Acad. Sci. U.S.A. 79 (1982).

(List continued on next page.)

Primary Examiner—Robert A. Wax
Assistant Examiner—Mindy B. Fleisher
Attorney, Agent, or Firm—Andrus, Sceales, Starke & Sawall

[57] ABSTRACT

The present invention is directed to a product and process for characterizing the human genome utilizing polymorphic DNA fragments containing (dC-dA)$_n$·(dG-dT)$_n$. The process comprises identifying polymorphic DNA fragments containing the above tandem repeat sequence followed by characterizing admixtures of genomic material by amplification of fragments containing the tandem repeat sequence using substantially unique and non-polymorphic primer sequences and appropriate separation of the so amplified fragments.

9 Claims, 6 Drawing Sheets

OTHER PUBLICATIONS

Hamada, et al., "Characterization of Genomic Poly(d-T-dG)·Poly (dC-dA) Sequences: Structure, Organization, and Conformation", Molecular and Cellular Biology, Dec. 1984, pp. 2610-2621.

Hamada, et al., "Enhanced Gene Expression by the Poly (dT-dG)·Poly (dC-dA), Sequence", Molecular and Cellular Biology, Dec. 1984, pp. 2622-2630.

Jeffreys, et al., "Spontaneous Mutation Rates to New Length Alleles at Tandem-Repetitive Hypervariable Loci in Human DNA", Nature vol. 332, Mar. 17, 1988.

Jeffreys, et al., "Hypervariable 'Minisatellite' Regions in Human DNA", Nature, vol. 314 Mar. 7, 1985.

Miesfeld, et al., "A Member of a New Repeated Sequence Family Which is Conserved Throughout Eucaryotic Evolution is Found Between the Human $\delta$ and $\beta$ Globin Genes", Nucleic Acids Research, vol. 9, #22, 1981.

Mullis, et al., "Specific Synthesis of DNA in Vitro via a Polymerase-Catalyzed Chain Reaction", Methods in Enzymology, vol. 155, 1987.

Nakamura, et al., "Variable Number of Tandem Repeat (VNTR) Markers for Human Gene Mapping", Science, vol. 235, Mar. 27, 1987.

Nordheim, et al., "The Sequence $(dC-dA)_n \cdot (dG-dT)_n$ Forms Left-Handed Z-DNA in Negatively Supercoiled Plasmids", Proc. Natl. Acad. Sci. U.S.A., vol. 80, pp. 1821-1825, Apr. 1983.

Overhauser, et al., "Identification of 28 DNA Fragments That Detect RFLPs in 13 Distinct Physical Regions of the Short Arm of Chromosome 5", Nucleic Acids Research, vol. 15, #11, 1987.

Pardue, et al., "$(dC-dA)_n \cdot (dG-dT)_n$ Sequences Have Evolutionarily Conserved Chromosomal Locations in Drosophila with Implications for Roles in Chromosome Structure and Function", The EMBO Journal, vol. 6, #6, pp. 1781-1789, 1987.

Saiki, et al., "Enzymatic Amplification of $\beta$-Globin Genomic Sequences and Restriction Site Analysis for Diagnosis of Sickle Cell Anemia", Science, vol. 20, Dec. 1985.

Saiki, et al., "Primer-Directed Enzymatic Amplification of DNA with a Thermostable DNA Polymerase", Science, vol. 239, Jan. 29, 1988.

Schumm, et al., "Identification of More Than 500 RFLPs by Screening Random Genomic Clones", Am. J. Hum. Genet. 42:143-159, 1988.

Shen, et al., "Sequence of the Human Somatostatis I Gene", Science, vol. 224, Apr. 13, 1984.

Skolnick, et al., "Simultaneous Analysis of Multiple Polymorphic Loci Using Amplified Sequence Polymorphisms (ASPs)", Genomics 2, 273-279 (1988).

Slightom, et al., "Human Fetal$^G\gamma$ and $^A\gamma'$-Globin Genes: Complete Nucleotide Sequences Suggest That DNA Can be Exchanged Between These Duplicated Genes", Cell, vol. 21, 627-638, Oct. 1980.

Sun, et al., "Non-Alu Family Interspersed Repeats in Human DNA and Their Transcriptional Activity", Nucleic Acids Research, vol. 12, #6, 1984.

Tautz, et al., "Simple Sequences are Ubiquitous Repetitive Components of Eukaryotic Genomes", Nucleic Acids Research, vol. 12, #10, 1984.

LENGTH POLYMORPHISMS IN $(DC-DA)_n \cdot (DG-DT)_n$ SEQUENCES

BACKGROUND AND FIELD OF THE INVENTION

The invention relates to polynucleotides which comprise an abundant new class of DNA polymorphisms and to a method for analyzing these polymorphisms. The polymorphisms can be used to identify individuals such as in paternity and forensic testing, and can also be used to map genes which are involved in genetic diseases or in other economically important traits.

The vast majority of DNA in higher organisms is identical in sequence among different individuals (or more accurately among the chromosomes of those individuals). A small fraction of DNA, however, is variable or polymorphic in sequence among individuals, with the formal definition of polymorphism being that the most frequent variant (or allele) has a population frequency which does not exceed 99% (Gusella, J. F. (1986), *Ann. Rev. Biochem.* 55:831–854). In the past, polymorphisms were usually detected as variations in gene products or phenotypes such as human blood types. Currently, almost all polymorphisms are detected directly as variations in genomic DNA.

Analysis of DNA polymorphisms has relied on variations in the lengths of DNA fragments produced by restriction enzyme digestion. Most of these restriction fragment length polymorphisms (RFLPs) involve sequence variations in one of the recognition sites for the specific restriction enzyme used. This type of RFLP contains only two alleles, and hence is relatively uninformative. A second type of RFLP is more informative and involves variable numbers of tandemly repeated DNA sequences between the restriction enzyme sites. These polymorphisms called minisatellites or VNTRs (for variable numbers of tandem repeats) were developed first by Jeffreys (Jeffreys et al (1985), *Nature* 314:67–73).

Jeffreys has filed two European patent applications, 186,271 and 238,329 dealing with the minisatellites. The first Jeffreys' application ('271) identified the existence of DNA regions containing hypervariable tandem repeats of DNA. Although the tandem repeat sequences generally varied between minisatellite regions, Jeffreys noted that many minisatellites had repeats which contain core regions of highly similar sequences. Jeffreys isolated or cloned, from genomic DNA, polynucleotide probes comprised essentially of his core sequence (i.e., wherein the probe had at least 70% homology with one of his defined cores). These probes were found to hybridize with multiple minisatellite regions (or loci). The probes were found to be useful in forensic or paternity testing by the identification of unique or characteristic minisatellite profiles. The later Jeffreys' European patent application proposed the use of probes which were specific for individual minisatellites located at specific loci in the genome. One problem with the Jeffrey's approach is that some of the most highly variable and hence useful minisatellites are susceptible to significant frequencies of random mutation (Jeffreys et al (1988), *Nature* 332:278–281).

Other tandemly repeated DNA families, different in sequence from the Jeffreys minisatellites, are known to exist. In particular, $(dC-dA)_n \cdot (dG-dT)_n$ sequences have been found in all eukaryotes that have been examined. In humans there are 50,000–100,000 blocks of $(dC-dA)_n \cdot (dG-dT)_n$ sequences, with n ranging from about 15–30 (Miesfeld et al (1981), *Nucleic Acids Res.* 9:5931–5947; Hamada and Kakunaga (1982), *Nature* 298:396–398; Tautz and Renz (1984), *Nucleic Acids Res.* 12:4127–4138). Prior to the work of this invention, a number of different human blocks of $(dC-dA)_n \cdot (dG-dT)_n$ repeats had been cloned and sequenced, mostly unintentionally along with other sequences of interest. Several of these characterized sequences were analyzed independently from two or more alleles. In arriving at this invention, sequences from these different alleles were compared; variations in the number of repeats per block of repeats were found in several cases (Weber and May (1989), *Am. J. Hum. Genet.* 44:388–396) (incorporated herein by reference in its entirety). The majority of these cases were not noted in publications. Although three isolated research groups produced published notations of site specific differences in sequence length (Das et al (1987), *J. Biol. Chem.* 262:4787–4793; Slightom et al (1980), *Cell* 21:627–638; Shen and Rutter (1984), *Science* 224:168–171), none of the groups recognized nor appreciated the extent of this variability or its usefulness and none generalized the observation. The other groups also did not consider the use of $(dC-dA)_n \cdot (dG-dT)_n$ sequences as genetic markers and did not offer a method by which such polymorphisms might be analyzed.

SUMMARY OF THE INVENTION

It has been discovered that $(dC-dA)_n \cdot (dG-dT)_n$ sequences exhibit length polymorphisms and therefore serve as an abundant pool of potential genetic markers (Weber and May (1988), *Am. J. Hum. Genet.* 43:A161 (abstract); Weber and May (1989), *Am. J. Hum. Genet.* 44:388–396) (both incorporated herein by reference). Accordingly, as a first feature of the present invention, polynucleotides are provided consisting of a DNA fragment, preferably $\leq 300$ base pairs (bp) in length, containing one or more blocks of tandem dinucleotide repeats $(dC-dA)_n \cdot (dG-dT)_n$ where n is preferably $\geq 6$.

A further aspect of the invention is the provision of a method for analyzing one or more specific $(dC-dA)_n \cdot (dG-dT)_n$ polymorphisms individually or in combination, which involves amplification of a small segment(s) of DNA (containing the block of repeats and some non-repeated flanking DNA) starting with a DNA template using the polymerase chain reaction, and sizing the resulting amplified DNA, preferably by electrophoresis on polyacrylamide gels. In a preferred embodiment, the amplified DNA is labeled during the amplification reaction by incorporation of radioactive nucleotides or nucleotides modified with a non-radioactive reporter group.

A further aspect of the invention is the provision of primers for the amplification of the polymorphic tandemly repeated fragments. The primers are cloned, genomic or preferably synthesized and contain at least a portion of the non-repeated, non-polymorphic flanking region sequence.

A further aspect of the invention is the provision of a method for determining the sequence information necessary for primer production through the isolation of DNA fragments, preferably as clones, containing the $(dC-dA)_n \cdot (dG-dT)_n$ repeats, by hybridization of a synthetic, cloned, amplified or genomic probe, which contains a sequence that is substantially homologous to the tandemly repeated sequence $(dC-dA)_n \cdot (dG-dT)_n$, to the DNA fragment. In a preferred embodiment the probe would be labeled, e.g., end labelling, internal labeling or nick translation.

In a more particular aspect of the present invention, some or all of the polynucleotide primers are $^{32}P$ or $^{35}S$ labeled in any conventional manner, such as end labeling, interior labeling, or post reaction labeling. Alternative methods of labeling are fully within the contemplation of the invention such as biotin labeling or possibly enzyme labeling (Matthews and Kricka (1988), *Anal. Biochem.* 169:1-25).

DETAILED DESCRIPTION OF THE PREFERRED EMBODIMENTS

Development of a polymorphic DNA marker based on length variations in blocks of $(dC-dA)_n.(dG-dT)_n$ repeats involves the following steps. First the sequence of a segment of DNA containing the repeats must be determined. This is accomplished most commonly by selecting a genomic DNA clone through hybridization to synthetic poly(dC-dA).poly(dG-dT) and then subsequently sequencing that clone. This same step can also be accomplished simply by selecting a suitable sequence from the literature or from one of the DNA sequence databases such as GenBank. The later approach is severely limited by the relatively small number of $(dC-dA)_n.(dG-dT)_n$ sequences that have been published. Second, once the sequence to be used is in hand, a pair of appropriate primers can be synthesized which are at least partially complementary to non-repeated, non-polymorphic sequences which flank the block of dinucleotide repeats on either side. Third, these primer pairs are used in conjunction with a genomic DNA (or occasionally cloned DNA) template to amplify a small segment of DNA containing the repeats using the polymerase chain reaction (Saiki et al (1985), *Science* 230:1350-1354 and U.S. Pat. No. 4,683,202, the substance of which is incorporated herein in its entirety). The DNA is preferably labeled during the amplification process by incorporating radioactive nucleotides. Fourth, the amplified DNA is resolved by polyacrylamide gel electrophoresis in order to determine the sizes of these fragments and hence the genotypes of the genomic DNA donors.

To exemplify the informativeness of the CA-GT repeats, sequences from 25 different human polymorphic markers of the type which can be used within the present invention, are listed in Table 1 in Example I. Each sequence represents only one allele at each specific locus. The first five sequences were taken from a computer search of GenBank; the remaining sequences were determined in the laboratory (see Example I). As can be seen in this compilation, the sequences exhibit substantial variation in the form of the tandem repeats. Some sequences, like for example markers Mfd3, Mfd17 and Mfd23, contain only CA-GT repeats with no imperfections. Other sequences, like for example Mfd2, Mfd7, Mfd13, and Mfd19 contain in addition to long runs of perfect CA-GT repeats, one or more imperfections in the run of repeats. These imperfections can be additional bases as in Mfd2 or more frequently GA-TC, AT-TA or CG-GC dinucleotide repeats as in Mfd7, Mfd13 and Mfd19. Homogenous runs of other dinucleotide repeats are often found in association with the CA-GT repeats like for example in Mfd5 and Mfd21. All of these repeat sequences can be used in this application.

Every human $(dC-dA)_n.(dG-dT)_n$ sequence with 11 or more repeats that has been tested by the invention has been found to be polymorphic (over 30 sequences to date). Since there are an estimated 50,000-100,000 $(dC-dA)_n.(dG-dT)_n$ blocks in the human genome, blocks are separated by an average spacing of 30,000-60,000 bp which is extremely tight in genetic terms. Two polymorphic markers spaced so that there is only 1% recombination between them are generally thought to be about $10^6$ bp apart; markers spaced only 50,000 bp apart on the average would be coinherited 99.95% of the time. This means that $(dC-dA)_n.(dG-dT)_n$ markers should find significant usage in the genetic mapping and clinical diagnosis of human genetic diseases, much as RFLPs have been used in the mapping and diagnosis of diseases such as cystic fibrosis (White and Lalouel (1988), *Ann. Rev. Genet.* 22:259-279).

The correspondence between polymorphisms (which are relatively rare in the genome) and the $(dC-dA)_n.(dG-dT)_n$ sequences is very strong evidence that the repeats are mainly, if not entirely, responsible for the sequence length variations. Further evidence comes from the fact that amplified polymorphic fragments containing the $(dC-dA)_n.(dG-dT)_n$ sequences always differ in size by multiples of 2 bp. Direct sequencing (see Example VI below) of allelic DNA also confirms this interpretation.

The informativeness of the $(dC-dA)_n.(dG-dT)_n$ polymorphisms is good to very good, with heterozygosities ranging from 34-91%. Most of the $(dC-dA)_n.(dG-dT)_n$ markers are therefore more informative than the two-allele RFLPs (Donis-Keller et al (1987), *Cell* 51:319-337; Schumm et al (1988), *Am. J. Hum. Genet.* 42:143-159). The number of alleles counted for the $(dC-dA)_n.(dG-dT)_n$ markers tested to date has ranged from 4-11. Relatively high numbers of alleles also improves the usefulness of these markers. Alleles tend to differ by relatively few numbers of repeats, with the result that all alleles for a single marker may span a range in size of 20 bp or less. This means that amplified fragments from several different markers can be analyzed simultaneously on the same polyacrylamide gel lanes, greatly improving the efficiency of the amplification process and the ability to identify individuals using the test.

In addition to the inherent useful properties of the $(dC-dA)_n.(dG-dT)_n$ markers, the use of the polymerase chain reaction to analyze the markers offers substantial advantages over the conventional blotting and hybridization used to type RFLPs. One of these advantages is sensitivity. Whereas microgram amounts of DNA are generally used to type RFLPs, ten nanograms of genomic DNA is sufficient for routine genotyping of the $(dC-dA)_n.(dG-dT)_n$ block markers (FIG. 3), and the polymerase chain reaction has recently been described as capable of amplifying DNA from a single template molecule (Saiki et al (1988), *Science* 239:487–491). Enough DNA can be isolated from a single modest blood sample to type tens of thousands of $(CA)_n$ block markers. Another advantage of the polymerase chain reaction is that the technique can be partially automated. For example, several commercial heating blocks are available which can automatically complete the temperature cycles used for the polymerase reaction. Automatic amplification reactions and the capability to analyze hundreds of markers on each polyacrylamide gel mean that the $(dC-dA)_n.(dG-dT)_n$ markers can be analyzed faster than RFLPs and are more readily usable in practical applications such as identity testing.

The practical outer limits of the length of the amplified DNA fragment is generally limited only by the resolving power of the particular separation system employed. The thin denaturing gels used in the work leading to this application are capable of resolving fragments differing by as little as 2 bases up to a total fragment length of about 300 bp. Use of longer gels and longer electrophoresis times could extend the resolving power up to perhaps 600 bp or even more. However the longer the fragment the lower the proportion of its length will be made up of the $(dC-dA)_n.(dG-dT)_n$ sequences, and hence the more difficult the resolution.

One specific application for the present invention is in the identification of individual humans such as in paternity and maternity testing, immigration and inheritance disputes, zygosity testing in twins, tests for inbreeding in man, evaluation of the success of bone marrow transplantation, quality control of human cultured cells, identification of human remains, and testing of semen samples, blood stains, and other material in forensic medicine. In this application, the ability to run numerous markers in a single amplification reaction and gel lane gives this procedure the possibility of extreme efficiency and high throughput.

Another specific application would be in human genetic analysis, particularly in the mapping through linkage analysis of genetic disease genes and genes affecting other human traits, and in the diagnosis of genetic disease through coinheritance of the disease gene with one or more of the polymorphic $(dC-dA)_n.(dG-dT)_n$ markers.

A third specific application contemplated for the present invention is in commercial animal breeding and pedigree analysis. All mammals tested for $(dC-dA)_n.(dG-dT)_n$ sequences have been found to contain them (Gross and Garrard (1986), *Mol. Cell. Biol.* 6:3010–3013). Also, as a byproduct of efforts to develop $(dC-dA)_n.(dG-dT)_n$ markers specific for human chromosome 19 from a library developed from a hamster-human somatic cell hybrid, several hamster $(dC-dA)_n.(dG-dT)_n$ markers have been developed (Weber and May (1989), *Am. J. Hum. Genet.* 44(3):388–396).

A fourth specific application is in commercial plant breeding. Traits of major economic importance in plant crops can be identified through linkage analysis using polymorphic DNA markers. The present invention offers an efficient new approach to developing such markers for various plant species.

It is also contemplated that the present invention and method of characterization could be easily extended to include other tandemly repeated simple sequences which may be polymorphic. Examples include $(dG-dA)_n.(dC-dT)_n$, $(dT-dA)_n.(dA-dT)_n$, and even $(dA)_n.(dT)_n$.

EXAMPLES

Example I

This example describes the method used to identify and isolate specific (dC-dA) fragments.

General Procedure

Total human genomic DNA or total DNA from a chromosome 19-specific large insert page library (LL19NL01) was digested to completion with Sau3A I, Alu I, Taq I, or a combination of Sau3A I and Taq I. DNA fragments ranging in size from about 150 to 400 base pairs were purified by preparative agarose gel electrophoresis (Weber et al (1988), *J. Biol. Chem.* 263:11321–11425), and ligated into mp18 or mp19 m13 vectors. Nitrocellulose plaque lifts (Benton and Davis (1977), *Science* 196:180–182) prepared from the resulting clones were screened by hybridization to synthetic poly(dC-dA).poly(dG-dT) which had been nick-translated using both $\alpha^{32}$P-dATP and $\alpha^{32}$P-dTTP to a specific activity of about $5 \times 10^7$ cpm/µg. Hybridizations were carried out in 6XSSC, pH 7.0, 2.5 mM EDTA, 5.0% (v/v) O'Darby Irish Cream Liqueur at 65°. After hybridization, filters were washed in 2XSSC, 25 mM NaPO$_4$, 0.10% SDS, 5.0 mM EDTA, 1.5 mM Na$_4$P$_2$O$_7$, pH 7.0, and then in 1SSC, 0.10% SDS, 5.0 mM EDTA, pH 7.0. Phage from the first screen were usually diluted and then screened a second time to insure plaque purity. Single stranded DNA was isolated from the positive clones and sequenced as described (Biggin et al (1983), *Proc. Natl. Acad. Sci. USA* 80:3963–3965).

GenBank DNA databases were screened for the presence of sequences with $(dC-dA)_6$ or $(dG-dT)_6$ using the QUEST program made available by Intelligenetics Inc. through the national BIONET computing network. Since the sequences of only one of the two strands of each DNA fragment are compiled in GenBank, separate screens for both CA and GT repeats are necessary.

Results

The hybridization procedure was used to isolate and sequence over one hundred $(dC-dA)_n.(dG-dT)_n$ blocks and the DNA immediately flanking the repeats. Examples are listed in Table 1 (Mfd6-25). Numbers of CA-GT dinucleotide repeats within the blocks ranged from 10 to over 30. Many of the blocks had imperfect repeats or were adjacent to tandem repeats with different sequences.

$(dC-dA)_n.(dG-dT)_n$ sequences obtained from the GenBank screens (Mfd1-5) were similar to those obtained through the hybridization procedure, except that sequences containing as few as six repeats could be selected.

plasmid DNA sample was amplified starting with 50 pg of total plasmid DNA as template.

Figure 2:
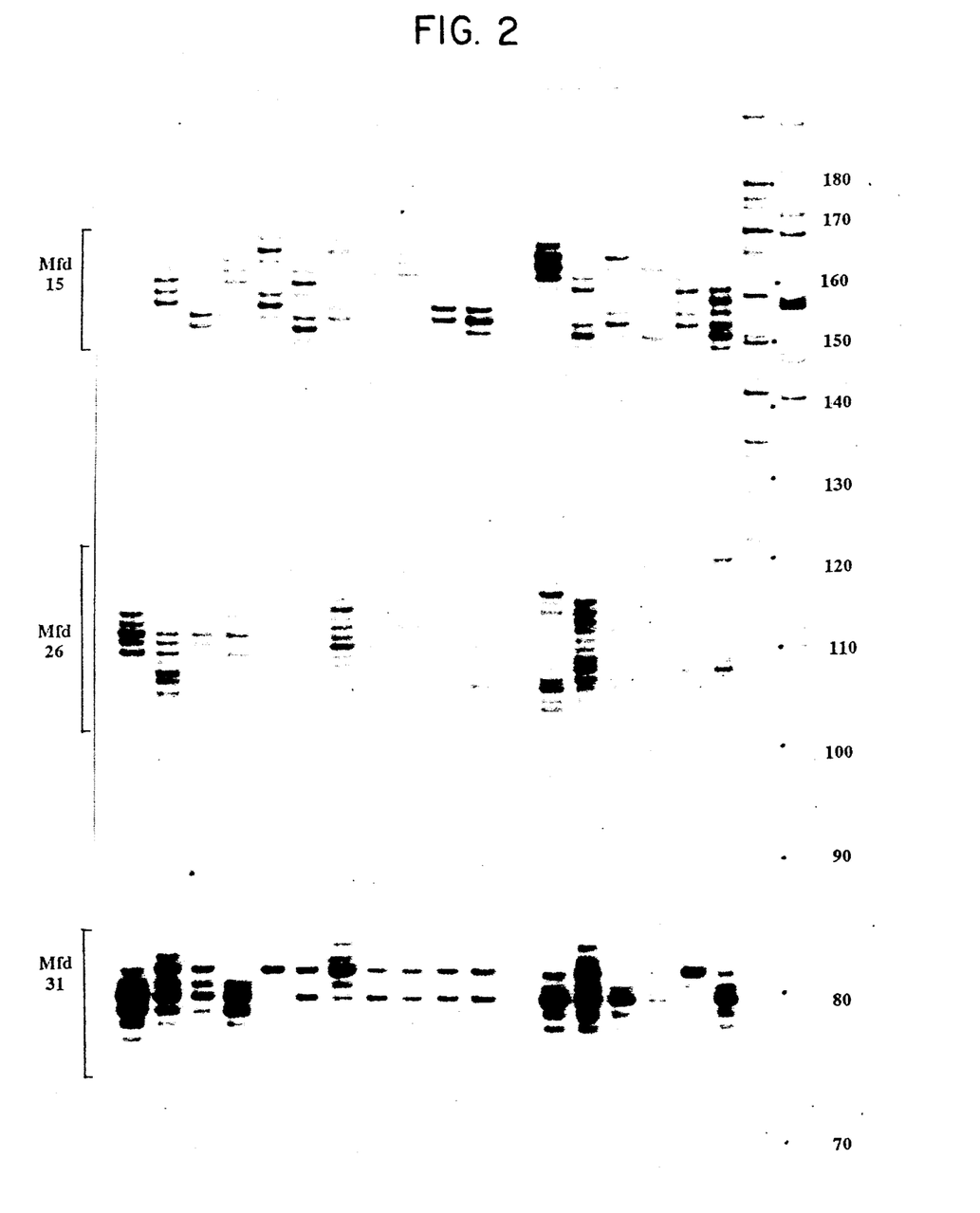
FIG. 2 is an additional example of length polymorphisms in amplified fragments containing $(dC-dA)_n.(dG-dT)_n$ sequences. Shown is an autoradiograph of a polyacrylamide gel.

Primers for the Mfd15 marker shown in FIG. 2 are

TABLE 1

| Marker | Repeat Sequence | Primer Sequences |
|---|---|---|
| Mfd1 | CATA(CA)$_{19}$ | GCTAGCCAGCTGGTGTTATT: ACCACTCTGGGAGAAGGGTA |
| Mfd2 | (AC)$_{13}$A(AC)$_{17}$A | CATTAGGATGCATTCTTCTG: GTCAGGATTGAACTGGGAAC |
| Mfd3 | (CA)$_{16}$C | GGTCTGGAAGTACTGAGAAA: GATTCACTGCTGTGGACCCA |
| Mfd4 | (AC)$_{12}$GCACAA(AC)$_{13}$A | GCTCAAATGTTTCTGCAACC: CTTTGTAGCTCGTGATGTGA |
| Mfd5 | (CT)$_7$(CA)$_{23}$ | CATAGCGAGACTCCATCTCC: GGGAGAGGGCAAAGATCGAT |
| Mfd6 | (CA)$_5$AA(CA)$_{13}$ | TCCTACCTTAATTTCTGCCT: GCAGGTTGTTTAATTTCGGC |
| Mfd7 | (CA)$_{20}$TA(CA)$_2$ | GTTAGCATAATGCCCTCAAG: CGATGGAGTTTATGTTGAGA |
| Mfd8 | (AC)$_{20}$A | CGAAAGTTCAGAGATTTGCA: ACATTAGGATTAGCTGTGGA |
| Mfd9 | (CA)$_{17}$ | GATGTCTCCTTGGTAAGTTA: AATACCTAGGAAGGGGAGGG |
| Mfd10 | (AC)$_{14}$A | CATGCCTGGCCTTACTTGC: AGTTTGAGACCAGCCTGCG |
| Mfd11 | (AC)$_{23}$A | ACTCATGAAGGTGACAGTTC: GTGTTGTTGACCTATTGCAT |
| Mfd12 | (AC)$_{11}$AT(AC)$_8$A | GGTTGAGATGCTGACATGC: CAGGGTGGCTGTTATAATG |
| Mfd13 | (CA)$_4$CGCG(CA)$_{19}$C | TTCCCTTTGCTCCCCAAACG: ATTAATCCATCTAAAAGCGAA |
| Mfd14 | (AC)$_{23}$A | AAGGATATTGTCCTGAGGA: TTCTGATATCAAAACCTGGC |
| Mfd15 | (AC)$_{25}$ | GGAAGAATCAAATAGACAAT: GCTGGCCATATATATATTTAAACC |
| Mfd16 | G(CG)$_4$(CA)$_5$TA(CA)$_3$(TA)$_2$(CA)$_6$CCAA(CA)$_{21}$ | AGAGATTAAAGGCTAAATTC: TTCGTAGTTGGTTAAAATTG |
| Mfd17 | (AC)$_{23}$ | TTTCCACTGGGGAACATGGT: ACTCTTTGTTGAATTCCCAT |
| Mfd18 | (AC)$_{18}$ | AGCTATCATCACCCTATAAAAT: AGTTTAACCATGTCTCTCCCG |
| Mfd19 | (AC)$_8$AG(AC)$_3$AG(AC)$_{24}$TCAC(TC)$_6$T | TCTAACCCTTTGGCCATTTG: GCTTGTTACATTGTTGCTTC |
| Mfd20 | (AC)$_{17}$ | TTTGAGTAGGTGGCATCTCA: TTAAAATGTTGAAGGCATCTTC |
| Mfd21 | (TA)$_6$TT(TA)$_2$TC(TA)$_5$TT(TA)$_3$CA(TA)$_7$(CA)$_8$TACATG(TA)$_3$ | GCTCAGGAGTTCGAGATCA: CACCACACCCGACATTTTA |
| Mfd22 | (TA)$_4$(CATA)$_2$(CA)$_{20}$(GA)$_2$(CAGA)$_5$ | TGGGTAAAGAGTGAGGCTG: GGTCCAGTAAGAGGACAGT |
| Mfd23 | (AC)$_{20}$ | AGTCCTCTGTGCACTTTGT: CCAGACATGGCAGTCTCTA |
| Mfd24 | (AC)$_7$AGAG(AC)$_{14}$A | AAGCTTGTATCTTTCTCAGG: ATCTACCTTGGCTGTCATTG |
| Mfd25 | (CA)$_{11}$ | TTTATGCAGCGTATGGATA: CACCACCATTGATCTGGAAG |

Example II

In this example a subset of the sequences isolated and identified as in Example I were amplified and labeled using the polymerase chain reaction, and were then resolved on polyacrylamide gels to demonstrate length polymorphisms in these sequences.

General Procedures

Oligodeoxynucleotide primers were synthesized on a Cyclone DNA synthesizer (Biosearch, Inc., San Rafael, Calif. Primers were 19-22 total bases in length, and contained 7-11 G+C bases. Self-complementary regions in the primers were avoided.

Genomic DNA was isolated from nucleated blood cells as described (Aldridge et al (1984), Am. J. Hum. Genet. 36:546-564). Standard polymerase chain reactions (Saiki et al (1985), Science 230:1350-1354; Mullis and Faloona (1987), Method Enzymol. 155:335-350; Saiki et al (1988), Science 239:487-491) were carried out in a 25 μl volume containing 10-20 ng of genomic DNA template, 100 ng each oligodeoxynucleotide primer, 200 μM each dGTP, dCTP and dTTP, 2.5 μM dATP, 1-2 μCi of α$^{32}$P-dATP at 800 CI/mmole or α$^{35}$S-dATP at 500 Ci/mmole, 50 mM KCl, 10 mM Tris, pH 8.3, 1.5 mM MgCl$_2$, 0.01% gelatin and about 0.75 unit of Taq polymerase (Perkin Elmer Cetus, Norwalk, Conn.). Samples were overlaid with mineral oil and processed through 25 temperature cycles consisting of 1 min at 94° (denaturation), 2 min at 55° (annealing), and 2.5 min at 72° (elongation). The last elongation step was lengthened to 10 min.

Figure 1:
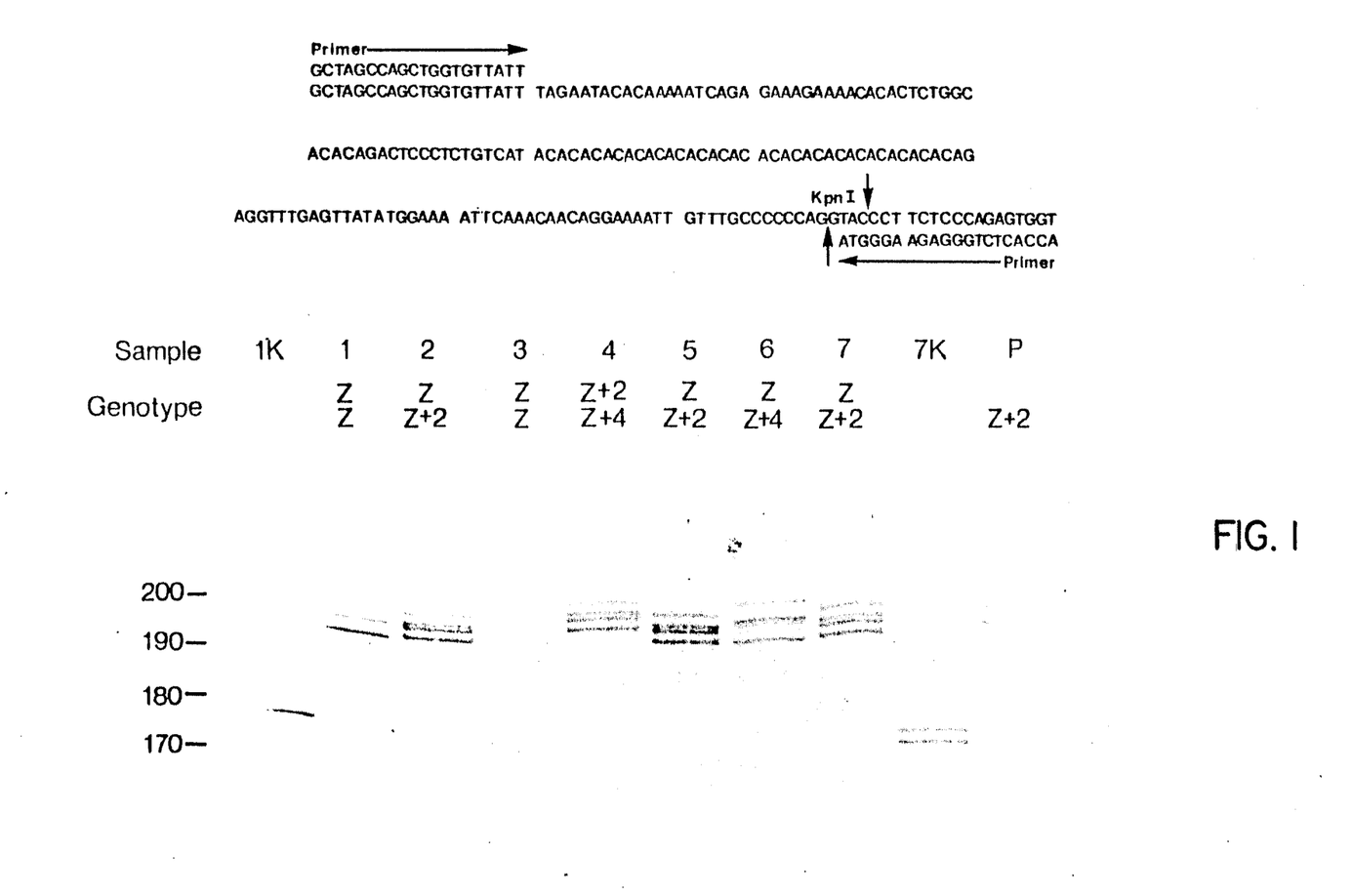
FIG. 1 is an example of a human $(dC-dA)_n.(dG-dT)_n$ polymorphism showing the sequence of the amplified DNA, the primers used in the amplification, and an autoradiograph of a polyacrylamide gel loaded with amplified DNA from this marker.

Results shown in FIG. 1 were obtained using conditions slightly different than the standard conditions. Templates were 100-200 ng of genomic DNA, annealing steps were 2.5 min at 37°, elongation steps were 3.5 min at 72°, and α$^{35}$S-dATP was added after the 18th cycle rather than at the beginning of the reactions. The listed in Table 1. Primers for the Mfd26 marker also shown in FIG. 2 are CAGAAAATTCTCTCTGG-CTA and CTCATGTTCCTGGCAAGAAT, and primers for the Mfd31 marker are TAATAAAG-GAGCCAGCTATG and ACATCTGATG-TAAATGCAAGT.

Aliquots of the amplified DNA were mixed with two volumes of formamide sample buffer and electrophoresed on standard denaturing polyacrylamide DNA sequencing gels. Gels were then fixed, dried and processed for autoradiography. Exposure times were about 2 days. Gel size standards were dideoxy sequencing ladders produced using m13, mp10 or mp8 DNA as template.

Results

FIG. 1 shows the amplified DNA fragments for the IGF1 (dC-dA)$_n$·(dG-dT)$_n$ marker in seven unrelated individuals (1-7). Z represents the most frequent allele; Z-2, the allele that is two bp larger than the most frequent; Z-2, the allele that is 2 bp smaller, etc. K indicates Kpn I digestion of amplified samples 1 and 7. Kpn digestions reduce the number of bands to half the original number because the CA strand, which normally migrates with an apparent size of about four bases less than the GT strand, is after Kpn I digestion, four bases longer than the GT strand resulting in comigration of the two strands. P refers to DNA amplified from a plasmid DNA sample containing the IGF1 (CA)$_n$ block. Sizes of the DNA fragments in bases are indicated on the left. At the top of the figure are shown the sequence of the amplified DNA along with the primer sequences and the site of Kpn I cleavage.

Because the CA and GT strands of the amplified DNA fragments migrate with different mobilities under the denaturing electrophoresis conditions (see Example III below), homozygotes yield two bands and heterozygotes four bands. The band corresponding to the faster moving CA strand is more intense on the autoradiographs than the band for the slower GT strand because the adenine content of the CA strand is higher and labeling is with $\alpha^{35}$S-dATP. Two of the seven individuals shown in FIG. 1 (1 and 3) were homozygous for the predominant allele (Z) of the IGF1 (CA)$_n$ block; the remainder were heterozygotes of various types.

Proof that the amplified DNA was really from the IGF1 gene and not from some other portion of the genome includes; that the amplified DNA was of the general expected size range for the primers used, that the amplified DNA hybridized to nick-translated poly(dC-dA).poly(dG-dT) (not shown), that this DNA was cleaved by a restriction enzyme, Kpn I, at the expected position (FIG. 1, lanes 1K and 7K), and that plasmid DNA containing the IGF1 sequence could be used as polymerase chain reaction template to yield DNA of the same size as was amplified from the genomic DNA templates (FIG. 1, lane P).

FIG. 2 shows additional examples of polymorphic amplified DNA fragments containing (dC-dA)$_n$.(dG-dT)$_n$ sequences. In this case three different markers fragments, Mfd15, Mfd26 and Mfd31 were amplified simultaneously from genomic DNA templates from several different individuals.

Example III

Comparison of different labeling approaches.

General Procedure

The ApoAII (Mfd3) CA or GT strand oligodeoxynucleotide primers were end-labeled for 1 h at 37° in a 50 μl reaction containing 90 pmoles (600 ng) of primer, 33 pmoles of $\gamma^{32}$P-ATP at 3000 Ci/mmole, 10 mM MgCl$_2$, 5 mM DTT, 50 mM Tris, pH 7.6, and 50 units of T4 polynucleotide kinase. Polymerase chain reactions were carried out in 25 μl volumes with 50 ng of end-labeled primer and 86 ng of each unlabeled primer. Interior labeling was performed as in Example II.

Results

Figure 3:
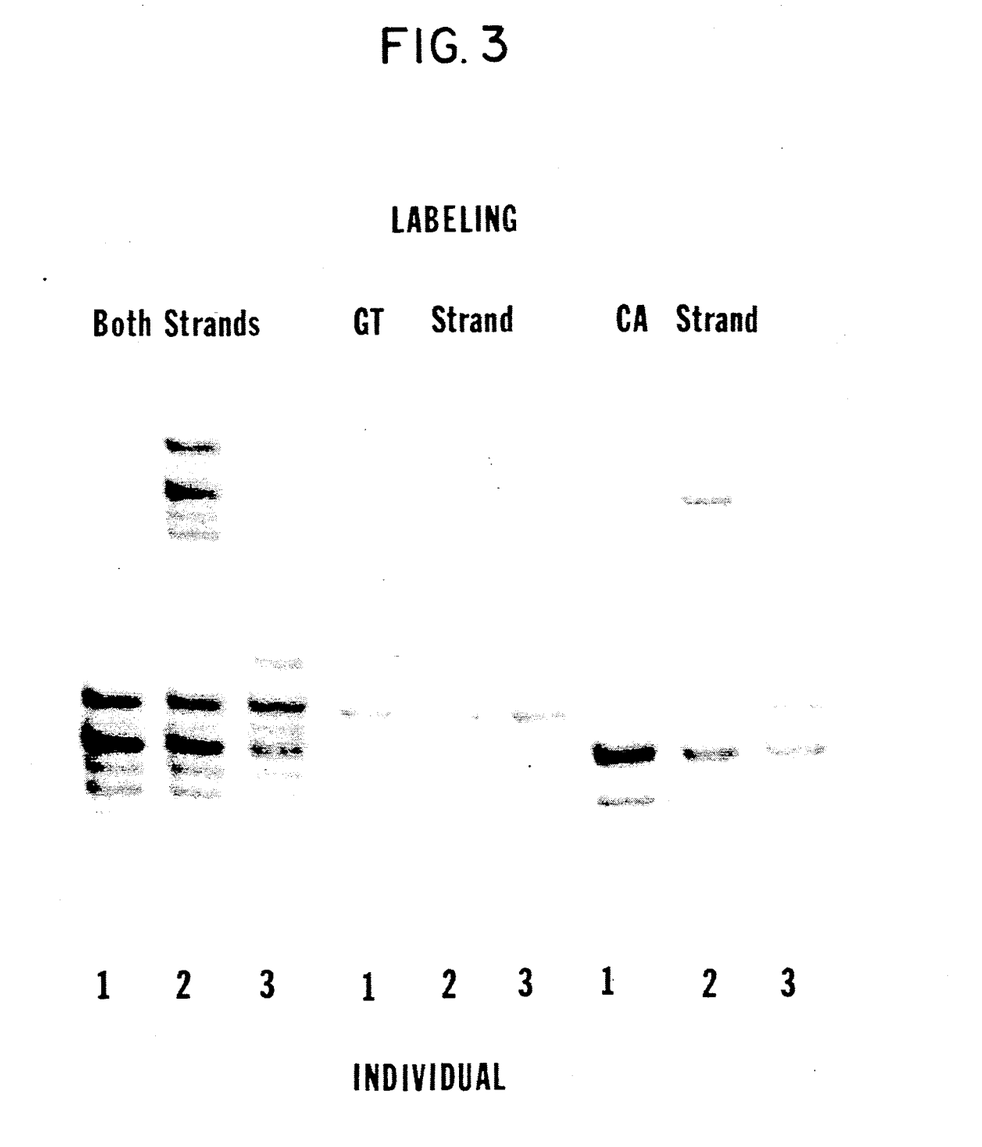
FIG. 3 is an autoradiograph of a polyacrylamide gel loaded with DNA amplified from the human Mfd3, ApoAII locus using DNA from three unrelated individuals as template and labeled through three different approaches: labeling the interiors of both strands with $\alpha^{32}P$-dATP, end-labeling the GT-strand primer with $^{32}P$ phosphate, or end-labeling the CA-strand primer with $^{32}P$ phosphate.

Rather than labeling the amplified DNA throughout the interiors of both strands, one or both of the polymerase chain reaction primers can be end-labeled using polynucleotide kinase. FIG. 3 shows the results of such an experiment using as template, DNA from three different individuals (1-3) and labeling throughout the interiors of both strands versus labeling of the GT strand primer only versus labeling of the CA strand primer only. Individual 1 is a homozygote and individuals 2 and 3 are heterozygotes. Note that because of strand separation during the denaturing gel electrophoresis labeling of both strands produces two major bands per allele on the autoradiograph, whereas labeling of the GT strand primer gives predominantly only the upper band for each allele and labeling the CA strand primer gives predominantly only the lower band for each allele. Additional fainter bands on the autoradiograph are artifacts of the polymerase chain reaction and will be discussed in Example VI.

Example IV

Estimates of informativeness and allele frequencies for the (dC-dA)$_n$.(dG-dT)$_n$ markers.

General Procedure

Estimates of PIC (polymorphism information content) (Botstein et al (1980), *Amer. J. Hum. Genet.* 32:314–331) and heterozygosity were obtained by typing DNA from 41–45 unrelated Caucasians for markers Mfd1–Mfd4, or by typing DNA From 75–78 parents of the 40 CEPH (Centre d'Etude du Polymorphisme Humain, Paris, France) reference families for markers Mfd5–Mfd10. The CEPH families are from the U.S.A., France, and Venezuela. Estimates of allele frequencies were calculated from the same data.

Results

PIC and heterozygosity values for the first ten (dC-dA)$_n$.(dG-dT)$_n$ markers are shown in Table 2. Values ranged from 0.31 to 0.80 with average PIC of 0.54±0.14 and average heterozygosity of 0.56±0.15. The informativeness of the (CA)$_n$ block markers is generally superior to standard unique sequence probe polymorphisms (Gilliam et al (1987), *Nucleic Acids Res.* 15:1445-1458; Overhauser et al (1987), *Nucleic Acids Res.* 15:4617-4627; Schumm et al (1988), *Am. J. Hum. Genet.* 42:143-159) and as good as many minisatellite polymorphisms (Nakamura et al (1987), *Science* 235:1612-1622). Considering the vast number of (CA)$_n$ blocks in the human genome, it is likely that a subset of up to several thousand can be identified with average heterozygosities of 70% or better.

The number of different alleles detected for the first ten markers (Table 2) ranged from 4 to 11. Alleles always differed in size by multiples of two bases (from CA strand to CA strand bands), consistent with the concept that the number of tandem dinucleotide repeats is the variable factor. Allele frequencies for the first ten markers are shown in Table 3. For most of the test markers, major alleles were clustered in size within about 6 bp on either side of the predominant allele. Amplified fragments must be small enough so that alleles differing in size by as little as two bases can easily be resolved on the polyacrylamide gels. The size differences between the largest and smallest alleles were <20 bp for most of the markers, and therefore several markers can be analyzed simultaneously on the same gel lane (see FIGS. 2 and 4).

TABLE 2

| | | Informativeness of (dC-dA)$_n$.(dG-dT)$_n$ Markers | | | | |
|---|---|---|---|---|---|---|
| Marker[a] | Chromosome Location | Length of Amplified DNA[b] | Repeat Sequence[c] | Number of Alleles | Hetero-zygosity | PIC[d] |
| Mfd1 | 12q22-q24.1 | 192 bp | CATA(CA)$_{19}$ | 5 | 54% | 0.53 |
| Mfd2 | 3q21-qter | 120 bp | (CA)$_{13}$A(CA)$_{17}$ | 4 | 34% | 0.31 |
| Mfd3 | 1q21-q23 | 137 bp | (AC)$_{16}$ | 6 | 74% | 0.65 |
| Mfd4 | 3q28 | 169 bp | (AC)$_{12}$GCACAA(AC)$_{13}$ | 6 | 51% | 0.46 |
| Mfd5 | 19q12-q13.2 | 151 bp | (CT)$_7$(CA)$_{23}$ | 11 | 80% | 0.79 |
| Mfd6 | — | 192 bp | (CA)$_5$AA(CA)$_{13}$ | 7 | 49% | 0.50 |
| Mfd7 | — | 213 bp | (CA)$_{20}$TA(CA)$_2$ | 6 | 54% | 0.51 |
| Mfd8 | — | 185 bp | (AC)$_{20}$ | 8 | 58% | 0.58 |
| Mfd9 | 19[e] | 100 bp | (CA)$_{17}$ | 9 | 72% | 0.69 |

TABLE 2-continued

| | | Informativeness of $(dC-dA)_n \cdot (dG-dT)_n$ Markers | | | | |
|---|---|---|---|---|---|---|
| Marker[a] | Chromosome Location | Length of Amplified DNA[b] | Repeat Sequence[c] | Number of Alleles | Hetero-zygosity | PIC[d] |
| Mfd10 | 19 | 138 bp | $(AC)_{14}$ | 6 | 39% | 0.42 |

[a]Mfd stands for Marshfield. The marker name substitutes for the probe name in RFLP markers and denotes a specific pair of amplification primers for each locus.
[b]Sizes of amplified DNA fragments corresponded to the predominant allele for each marker. Estimated error is 2 bp.
[c]Sequences for Mfd1–Mfd5 were taken from GenBank. Sequences for Mfd6–Mfd10 were determined in the laboratory.
[d]PIC is Polymorphism Information Content (Botstein et al (1980), Am. J. Hum. Genet. 32:314-331).
[e]Markers 9 and 10 were developed using clones selected from a chromosome 19-specific phage library.

TABLE 3

Allele Frequencies for $(dC-dA)_n \cdot (dG-dT)_n$ Markers

| Allele[a] | Marker | | | | | | | | | |
|---|---|---|---|---|---|---|---|---|---|---|
| | 1 | 2 | 3 | 4 | 5 | 6 | 7 | 8 | 9 | 10 |
| Z + 14 | —[b] | — | — | — | 1% | — | — | — | — | — |
| Z + 10 | — | — | — | — | — | 3% | — | 1% | — | — |
| Z + 8 | — | — | 3% | — | 3% | 11% | — | 3% | — | — |
| Z + 6 | — | — | 35% | 2% | 4% | 1% | — | 7% | 3% | 1% |
| Z + 4 | 18% | 6% | — | 6% | 15% | 1% | 6% | 2% | 1% | — |
| Z + 2 | 16% | 11% | 1% | 13% | 15% | 3% | 4% | 27% | 12% | 5% |
| Z | 60% | 81% | 39% | 70% | 34% | 64% | 66% | 54% | 38% | 73% |
| Z − 2 | 5% | 2% | — | 1% | 3% | 18% | 15% | 4% | 6% | — |
| Z − 4 | — | — | 8% | — | 2% | — | 7% | 1% | 4% | 10% |
| Z − 6 | — | — | 14% | 8% | 1% | — | — | — | 4% | 9% |
| Z − 8 | — | — | — | — | — | — | 2% | — | 31% | 1% |
| Z − 12 | — | — | — | — | — | — | — | — | 1% | — |
| Z − 14 | — | — | — | — | 11% | — | — | — | — | — |
| Z − 16 | 1% | — | — | — | — | — | — | — | — | — |
| Z − 22 | — | — | — | — | 12% | — | — | — | — | — |
| Spread[c] (bp) | 20 | 6 | 14 | 12 | 36 | 12 | 12 | 14 | 18 | 14 |

[a]Z indicates the predominant allele for each marker.
[b]A dash means this allele was not found.
[c]Spread is the size difference between amplified DNA fragments corresponding to largest and smallest alleles.

Example V

Demonstration of Mendalian codominant inheritance of $(dC-dA)_n \cdot (dG-dT)_n$ markers.

General Procedure

DNA from individuals of the CEPH families and from other three generation families was used as template for the amplification of various $(dC-dA)_n \cdot (dG-dT)_n$ markers using the procedure described in Example II.

Results

Figure 4:
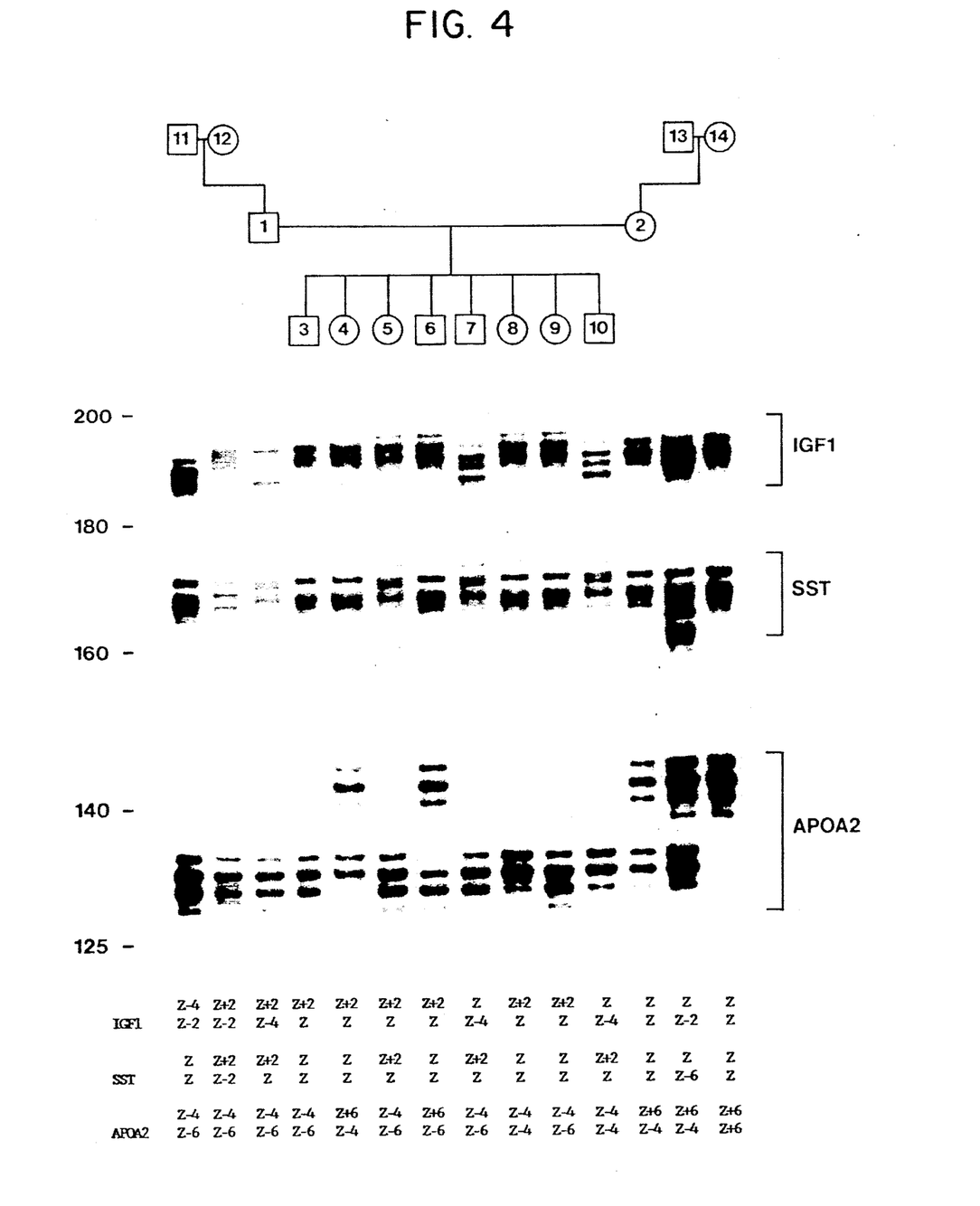
FIG. 4 is an example of the Mendelian inheritance of three different human $(dC-dA)_n.(dG-dT)_n$ markers through three generations. Shown are the pedigree of this family, an autoradiograph of a gel loaded with the amplified DNA and a list of the genotypes of the individual family members.

FIG. 4 shows the amplified DNA from markers Mfd1, Mfd3 and Mfd4 from CEPH family 1423. DNA fragment sizes in bases are marked to the left of the gel. Individual genotypes are listed below the gel. All three markers showed Mendelian behavior for this family.

A total of approximately 500 family/marker combinations have been tested to date. Mendelian codominant inheritance has been observed in all cases; no new mutations have been found. Therefore new mutations are unlikely to be a general problem with the $(dC-dA)_n \cdot (dG-dT)_n$ markers.

Example VI

Artifacts of the amplification reactions.

General Procedure

Aliquots of two different $(dC-dA)_n \cdot (dG-dT)_n$ amplified fragments (two different markers from two individuals), untreated from the polymerase chain reaction (C), were brought up to 200 μM dATP and then incubated at 37° for 30 min with 6 units of Klenow enzyme (K), 1 unit of T4 DNA polymerase (P), or with no additional enzyme (T). Samples were then mixed with formamide sample buffer and loaded on polyacrylamide gels.

Figure 6:
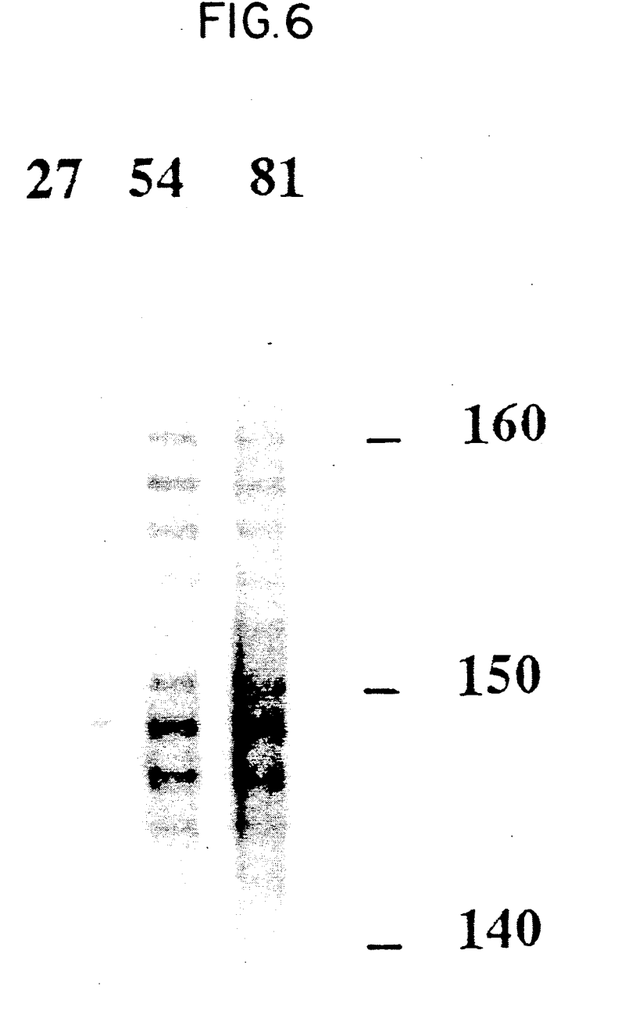
FIG. 6 is an autoradiograph showing the effect of additional polymerase chain reaction cycles on amplified DNA for the Mfd3 marker from a single individual.

For the results shown in FIG. 6, DNA from an individual with the Mfd3 genotype Z+6, Z−6 was amplified with modified Mfd3 primers (AGGCTGCAG-GATTCACTGCTGTGGACCCA and GTCGGTACCGGTCTGGAAGTACTGAGAAA) so that sites for the restriction enzymes Pst I and Kpn I were located at opposite ends of the amplified DNA. An aliquot of the amplified DNA from a 27 cycle reaction was diluted 60,000 fold with 0.2X TE, and 10 μl of the dilution (approximately $10^5$ molecules) were amplified with the same primers for another 27 cycles. An aliquot of the second amplification reaction was diluted as above and subjected to a third 27 cycle reaction. Amplified DNA samples were treated with T4 DNA polymerase prior to electrophoresis.

Amplified DNA from the first reaction described in the above paragraph was digested with Kpn I and Pst I, extracted with phenol, and simultaneously concentrated and dialyzed into 0.2X TE using a Centricon 30 cartridge. This DNA was then ligated into mp19 and transformed into E. coli. Clear plaques on X-gal/IPTG plates from the transformed cells were picked, amplified and used to isolate single-stranded DNA. DNA from 102 such clones was sequenced. The distribution of the numbers of dinucleotide repeats in these clones is shown in Table 4.

Results

Additional bands, less intense than the major pair of bands for each allele and smaller in size than the major bands, were usually seen for the amplified DNA fragments. These bands are particularly apparent in FIGS.

2-4. The additional bands were present when cloned DNA versus genomic DNA was used as template (FIG. 1, lane P), and even when such small amounts of heterozygote genomic DNA were used as template that only one of the two alleles was amplified. Also, DNA amplified from 63 lymphocyte clones (gift of J. Nicklas) (Nicklas et al (1987), *Mutagenesis* 2:341-347) produced from two individuals showed no variation in genotype for all clones from a single donor. These results indicate that the additional bands are generated as artifacts during the amplification reactions, and are not reflections of somatic mosaicism.

Figure 5:
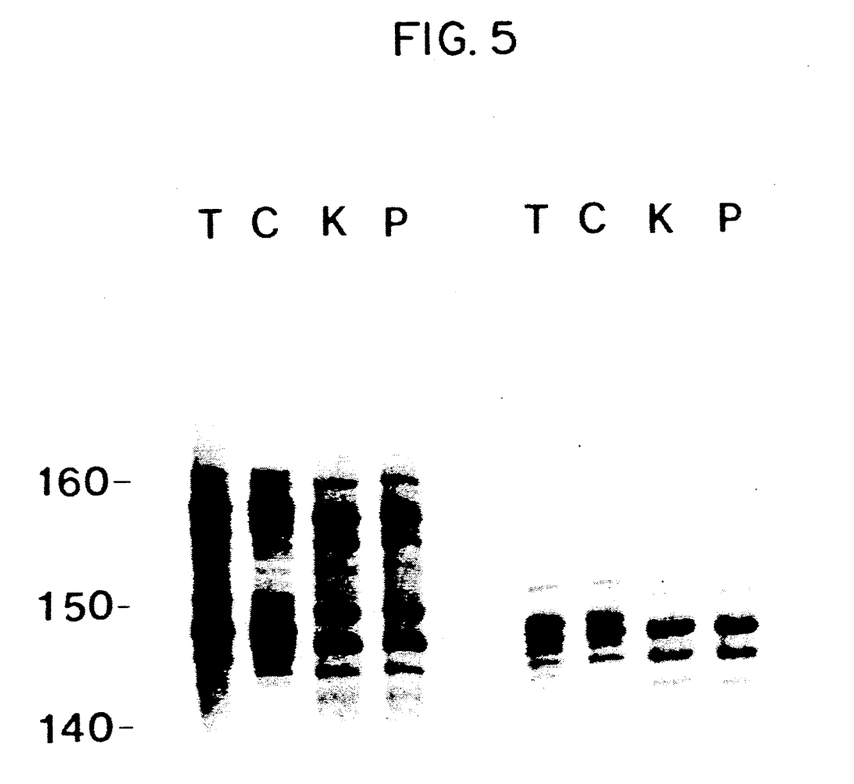
FIG. 5 is an autoradiograph showing treatment of amplified DNA containing $(dC-dA)_n.(dG-dT)_n$ sequences with either the Klenow fragment of DNA polymerase I or with T4 DNA polymerase.

Griffin et al. (1988), (*Am. J. Hum. Genet.* 43(Suppl.-):A185) recently demonstrated that DNA fragments amplified by the PCR could not be efficiently ligated to blunt ended vectors without first repairing the ends of the fragments with T4 DNA polymerase. To test whether "ragged" ends were responsible for the extra bands associated with $(dC-dA)_n.(dC-dT)_n$ amplified fragments, amplified DNA (C) was treated with the Klenow fragment of DNA polymerase I (K), with T4 DNA polymerase (P) or with no enzyme (T) as shown in FIG. 5. Both Klenow enzyme and T4 DNA polymerase simplified the banding pattern somewhat by eliminating extra bands which differed in size from the most intense bands by 1 base. These enzymes also reduced the size of the most intense bands by 1 base. The most likely explanation for these results is the Taq polymerase produces a mixture of fragments during the PCR with different types of ends. The most intense bands in the untreated samples are likely derived from double stranded molecules with single base noncomplementary 3' overhangs. The fainter bands which are 1 base smaller than the major bands are likely to be blunt ended. The 3'-5' exonuclease activity of Klenow or T4 DNA polymerase converts the molecules with overhangs into blunt ended molecules. Clark (1988), (*Nucleic Acids Res.* 16:9677) recently showed that a variety of DNBA polymerases including Taq polymerase can add a noncomplementary extra base to the 3' ends of blunt ended molecules.

Remaining after Klenow or T4 DNA polymerase treatment are extra bands which differ in size from the major bands by multiples of two bases. The data in Table 4 and FIG. 6 strongly indicate that these particular extra bands are the result of the skipping of repeats by the Taq polymerase during the amplification cycles. Sequencing of individual clones of DNA amplified for 27 cycles (first lane, FIG. 6) verifies that repeats have been deleted in the amplified DNA (Table 4). The largest of the predominant-sized fragments in the amplified DNA (with the exception of the one 20-mer) are 19 and 13 repeats in length, consistent with the $Z+6$, $Z-6$ genotype of the donor of the template DNA. Substantial numbers of clones containing fewer repeats are also seen, and this distribution matches the pattern of fragments shown in the first lane of FIG. 6. If the Taq polymerase is skipping repeats during the amplification cycles, as seems likely from the sequencing data, then further cycles of amplification in addition to the first 27 should reduce the intensities of the bands corresponding to the original DNA in the template and increase the intensities of the bands corresponding to fragments with skipped repeats. This is exactly what is observed in FIG. 6 for the amplified DNA from the reactions with 54 and 81 total amplification cycles.

TABLE 4

Distribution of numbers of repeats in clones of amplified DNA

| Number of Repeats | Number of Clones |
|---|---|
| 20 | 1 |
| 19 | 20 |
| 18 | 22 |
| 17 | 4 |
| 16 | 5 |
| 15 | 1 |
| 14 | 0 |
| 13 | 22 |
| 12 | 18 |
| 11 | 3 |
| 10 | 3 |
| 9 | 3 |

Example VII

Use of $(dC-dA)_n.(dG-dT)_n$ polymorphisms to identify individuals.

General Procedure

Genomic DNA from a collection of 18 unrelated individuals and from an unknown individual was isolated from blood and amplified with various $(dC-dA)_n.(dG-dT)_n$ markers as described under Example II. Genotype frequencies were calculated from the allele frequencies shown in Table 3 assuming Hardy-Weinberg equilibria.

Results

One individual out of a group of 18 unrelated volunteers was selected so that the identity of this individual was unknown. The unknown DNA sample and the control samples were then typed for the Mfd3 and Mfd4 markers. As shown in Table 5, only three of the 18 controls had Mfd3 and Mfd4 genotypes consistent with the unknown sample, namely, individuals 22, 35 and 42. Further typing of these three samples and the unknown with four additional markers as shown in Table 5, conclusively demonstrated that the unknown DNA sample came from individual 22.

Table 6 shows the expected genotype frequencies for the six typed markers for individual 22 using the allele frequency data from Table 3. Single genotypes range in frequency from 0.04 to 0.49. The frequency for the entire collection of six markers is the product of the individual probabilities or $1.5 \times 10^{-5}$ or about 1 in 65,000 people. Choosing a better, more informative collection of $(dC-dA)_n.(dG-dT)_n$ markers would result in considerably greater discrimination.

TABLE 5

Genotypes for identification test

| | Markers | | | | | |
|---|---|---|---|---|---|---|
| Indiv. | Mfd3 | Mfd4 | Mfd9 | Mfd1 | Mfd8 | Mfd11 |
| 7 | 137,137 | 169,171 | | | | |
| 8 | 131,137 | 169,169 | | | | |
| 10 | 131,143 | 169,169 | | | | |
| 11 | 131,143 | 169,163 | | | | |
| 12 | 143,133 | 169,173 | | | | |
| 14 | 137,143 | 169,169 | | | | |
| 22 | 137,137 | 169,169 | 98,92 | 194,192 | 187,185 | 108,116 |
| ukn | 137,137 | 169,169 | 98,92 | 194,192 | 187,185 | 108,116 |
| 23 | 139,143 | 169,167 | | | | |
| 25 | 137,143 | 169,163 | | | | |
| 26 | 133,143 | 169,171 | | | | |
| 27 | 143,143 | 169,169 | | | | |
| 30 | 137,143 | 169,171 | | | | |
| 31 | 137,143 | 169,169 | | | | |
| 33 | 137,143 | 169,171 | | | | |
| 34 | 143,143 | 169,169 | | | | |

TABLE 5-continued

Genotypes for identification test

| Indiv. | Mfd3 | Mfd4 | Mfd9 | Mfd1 | Mfd8 | Mfd11 |
|---|---|---|---|---|---|---|
| 35 | 137,137 | 169,169 | 100,92 | 192,192 | 185,183 | 108,108 |
| 41 | 137,131 | 169,171 | | | | |
| 42 | 137,137 | 169,169 | 104,100 | 192,192 | 185,185 | 120,108 |

TABLE 6

Genotype frequencies

| Marker | Genotype for #22 | Allele Frequency for #22 | Genotype* Frequency for #22 |
|---|---|---|---|
| Mfd3 | 137,137 | 39% 137 | 15% |
| Mfd4 | 169,169 | 70% 169 | 49% |
| Mfd9 | 98,92 | 6% 98, 31% 92 | 4% |
| Mfd1 | 192,194 | 60% 192, 16% 194 | 20% |
| Mfd8 | 185,187 | 54% 185, 27% 187 | 29% |
| Mfd11 | 108,116 | 43% 108, 10% 116 | 9% |
| | | Total = | 0.0015% |

*Homozygote genotype frequency = (allele frequency)$^2$
Heterozygote genotype frequency = 2(allele$_1$)(allele$_2$)

Various modes of carrying out the invention are contemplated as being within the scope of the following claims particularly pointing out and distinctly claiming the subject matter which is regarded as the invention.

I claim:

1. A method of analyzing or typing polymorphic DNA fragments which contain (dC-dA)$_n$.(dG-dT)$_n$ repeats which are specific to particular loci in the genome comprising:
   amplifying at least one polymorphic DNA fragment containing at least one (dC-dA)$_n$.(dG-dT)$_n$ segment using the polymerase chain reaction with a DNA sample which includes the said DNA fragment as a template, and with two oligonucleotide primers sufficiently complementary to non-repeated sequences at the ends of said fragment within said sample to hybridize therewith, and separating and characterizing amplified fragments on the basis of size.

2. The method of claim 1 further comprising labeling or marking said polymorphic DNA fragments.

3. The method of claim 1 wherein said primers are obtained by direct synthesis.

4. The method of claim 1 wherein said primers are end-labeled.

5. The method of claim 1 wherein more than one DNA fragment containing at least one segment of (dC-dA)$_n$.(dG-dT)$_n$ is amplified and characterized simultaneously.

6. The method of claim 1 used to establish the identity, pedigree, or relationship of an individual comprising comparison of said amplified fragments with amplified fragments from the DNA of one or more control individuals wherein the control DNA samples have been similarly amplified and characterized.

7. The method of claim 1 wherein the amplified fragments are separated and characterized by gel electrophoresis.

8. The method of claim 1 wherein the DNA sample is genomic DNA.

9. The method of claim 1 wherein the DNA sample is cloned DNA.

* * * * *